United States Patent [19]

Trouet et al.

[11] Patent Number: 4,831,038

[45] Date of Patent: May 16, 1989

[54] VINBLASTINE DERIVATIVES AND PHARMACEUTICAL COMPOSITION CONTAINING THEM

[75] Inventors: André Trouet, Winksele; Jean-Paul DeJonghe, Wavre; Marie-Paule Collard, Brussels; Bhushana K. S. P. Rao, Rosieres, all of Belgium

[73] Assignee: Ire-Celltarg S.A., Fleurus, Belgium

[21] Appl. No.: 2,895

[22] Filed: Jan. 13, 1987

[30] Foreign Application Priority Data

Jan. 13, 1986 [FR] France .............................. 86 00364
Dec. 12, 1986 [JP] Japan ................................. 86 17412

[51] Int. Cl.$^4$ .................. A61K 31/475; C07D 519/04
[52] U.S. Cl. ..................................... 514/283; 540/478
[58] Field of Search ......................... 540/478; 514/283

[56] References Cited

U.S. PATENT DOCUMENTS 4,203,898 5/1980 Cullinan et al. ...................... 540/478
4,388,305 6/1983 Trouet et al. ........................ 514/283
4,639,456 1/1987 Trouet et al. ........................ 514/283

FOREIGN PATENT DOCUMENTS 2400029 9/1979 France .

OTHER PUBLICATIONS

Richter Gedeon, Chemical Abstracts, vol. 97:216541c (1982).
Richter Gedeon, Chemical Abstracts, vol. 97:216542d (1982).

Primary Examiner—Donald G. Daus
Assistant Examiner—Diana G. Rivers
Attorney, Agent, or Firm—Fleit, Jacobson, Cohn & Price

[57] ABSTRACT

The invention relates to vinca (indole-dihydroindole) alkaloid derivatives, in which a fatty chain containing at least 7 aliphatic carbon atoms is present at least at the $C^3/C^4$-position.

The derivatives according to the present invention are useful as drugs.

7 Claims, No Drawings

VINBLASTINE DERIVATIVES AND PHARMACEUTICAL COMPOSITION CONTAINING THEM

The present invention relates to new vinblastine derivatives, to processes for preparing them and to the application of these compounds by way of a drug, in particular as an antitumor agent.

Vinblastine is a known antitumor alkaloid, isolated from *Vinca rosea*. Vinblastine (hereinafter designated "VLB" by reason of its old INN: vincaleukoblastine) has been the subject of many investigations, studies and patents, for the purpose of preparing more active, more selective and less toxic antitumor substances.

The present invention relates to vinca (indoledihydroindole) alkaloid derivatives, in which a fatty chain containing at least 7 aliphatic carbon atoms is present at least at the $C^3/C^4$-position.

Among the vinca alkaloid derivatives according to the present invention, the $C^3$- and $C^4$-derivatives of vinblastine, vincristine and vindesine must be mentioned; but other derivatives possessing antineoplastic activity can obviously be envisaged.

Among these derivatives, there must be mentioned the compounds of general formula I:

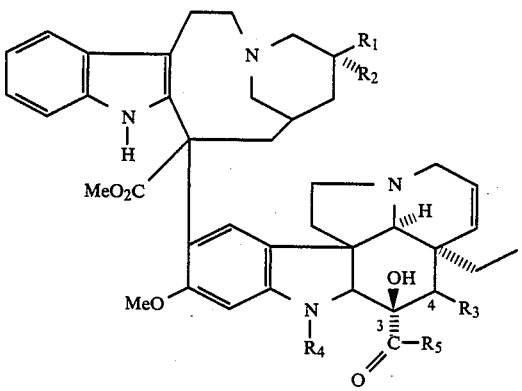

in which:
($R_1$, $R_2$) denote (—Et, —OH), or (—H, —Et),
$R_4$ denotes —H, —Me or —CHO,
$R_3$ denotes —OH or

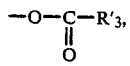

$R_5$ denotes —A—$R'_5$, A beng chosen from —NH—, —O—,

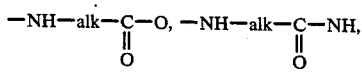

$R'_3$ and $R'_5$ denote an aliphatic hydrocarbon radical, at least one of $R'_3$ and $R'_5$ having at least 7 aliphatic carbon atoms, which is unsubstituted or substituted with one or more amino, di($C_1$-$C_3$ alkyl)amino, mono($C_1$-$C_3$ alkyl)amino, NH($C_2$-$C_5$ alkanoyl), cyano, COOH, S($C_1$-$C_3$ alkyl), COO($C_1$-$C_3$ alkyl) or COO-aryl radicals, alk denoting a linear or branched divalent hydrocarbon chain which can contain one or more substituents or groups, in particular OH, $NH_2$, $CO_2H$, or alternatively A is the protected or unprotected divalent radical derived from an amino acid which participates in the constitution of proteins and terminates in —NH and

or —NH and

Among aliophatic hydrocarbon radicals, the following radicals must be mentioned:

linear or branched $C_1$ to $C_{20}$ alkyl radicals, and linear or branched $C_1$ to $C_{20}$ alkenyl radicals, these radicals preferably being linear; when these radicals are substituted, this preferably occurs at the end of the chain.

Among radicals alk, there must be mentioned linear or branched $C_1$ to $C_7$, and preferably $C_1$ to $C_7$, hydrocarbon radicals which are unsubstituted or substituted with one or more OH, NH or COOH radicals.

When A is a divalent radical derived from an amino acid which participates in the constitution of proteins, it can be in D form or in L form when is contains an asymmetric carbon atom.

The radical A can originate from Gly, Ala, Val, Leu, Ile, Phe, Ser, Thr, Lys, Lys-OH, Arg, Asp, Asp-$NH_2$, Glu, Glu-$NH_2$, Cys-SH, Met, Tyr, Trp or His.

When these radicals possess groups other than the bonding groups, these can be protected by protective groups Pr known in protein chemistry, such as the Cbz, carbobenzoxy, group for example.

The term aryl preferably denotes a phenyl radical.

More especially, the subject of the invention is the derivatives corresponding to the general formula (A) in which:

$R_1$, $R_2$, $R_3$, $R_4$, $R'_3$ and $R'_5$ have the same meaning as above, but $R_5$ denotes A'—$R''_5$ with A' denoting a divalent radical derived from a natural amino acid in D or L form or from a natural amino acid dipeptide in D or L form, especially derived from Ile, Trp or Gly-Phe-, terminating in —NH and

$R''_5$ denotes —O—$R'_5$ or NH—$R'_5$.

Preferably, these derivatives are such that A' originates from an amino acid chosen from the group Ile, Trp and Gly-Phe, and $R'_5$ is a $C_{10}$ to $C_{16}$ hydrocarbon radical.

In a particular embodiment of the invention, $R_4$ denotes Me and $R_3$ denotes OH.

The present invention also relates to a process for preparing the compounds of general formula I and also to the pharmaceutical compositions comprising a compound of general formula I and an excipient, support or vector which is pharmaceutically acceptable.

The compounds of general formula I according to the invention can be divided into two groups, according to whether the fatty chain is in the $C^3$- or $C^4$-position.

Thus, on the one hand, the especially preferred vinca alkaloid derivatives are those which correspond to the formula I and in which:

$R_3$ denotes —OH, $R_5$ denotes —A—$R'_5$ with A chosen from —NH—,

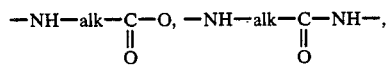

$R'_5$ denoting a $C_7$ to $C_{20}$ alkyl radical or alkenyl radical which is unsubstituted or substituted with one or more amino, di($C_1$-$C_3$ alkyl)amino, mono($C_1$-$C_3$ alkyl)amino, NH($C_2$-$C_5$ alkanoyl), cyano, COOH, S($C_1$-$C_3$ alkyl), COO($C_1$-$C_3$ alkyl) or COO-aryl radicals, alk denoting a $C_1$ to $C_3$ alkylene chain, or A is a protected or unprotected divalent radical derived from an amino acid which participates in the constitution of proteins.

When A denotes —NH—, $R'_5$ is preferably chosen from —$(CH_2)_{11}$—$CH_3$, —$(CH_2)_{17}$—$CH_3$, —$(CH_2)_{12}$—$NH_2$ or —$(CH_2)_7$—CH=CH—$(CH_2)_8$—$CH_3$.

Thus, for example, the compound corresponding to the following formula $I_3$:

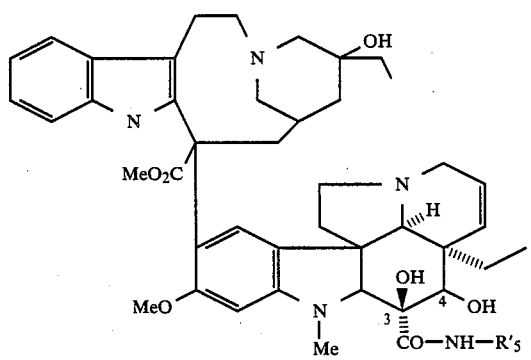

and in which $R'_5$ denotes —$(CH_2)_{11}$—$CH_3$, will be referred to as compound No. 91.

The compound corresponding to the same formula $I_3$ and in which $R'_5$ denotes —$(CH_2)_{12}$—$NH_2$ will be referred to as compound No. 182.

Similarly, the compound No. 252, will be that of formula $I_3$ in which $R'_5$ denotes —$(CH_2)_7$—CH=CH—$(CH_2)_8$—$CH_3$ When A denotes a protected or unprotected divalent radical derived from an amino acid which participates in the constitution of proteins, then $R'_5$ is preferably chosen from $C_7$ to $C_{20}$ alkyl radicals and $C_7$ to $C_{20}$ n-alkenyl radicals containing one or two double bonds.

Furthermore, other especially preferred vinca alkaloid derivatives according to the present invention are those which correspond to the general formula I and in which:

$R_5$ denotes —OMe, $R_3$ denotes

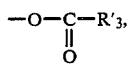

which $R'_3$ denoting a $C_7$ to $C_{20}$ alkyl or alkenyl radical which is unsubstituted or substituted with one or more amino, di($C_1$-$C_3$ alkyl)amino, mono($C_1$-$C_3$ alkyl)amino, NH($C_2$-$C_5$ alkanoyl), cyano, COOH, S($C_1$-$C_3$ alkyl), COO($C_1$-$C_3$ alkyl) or COO-aryl radicals.

Thus, in the following formula $I_4$:

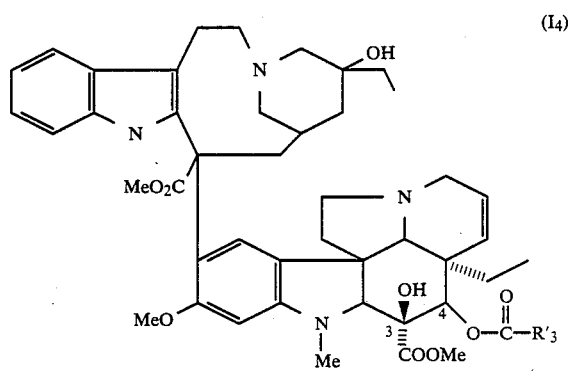

$R'_3$ is preferably chosen from: —$(CH_2)_{14}$—$CH_3$, —$CH_2CH(COOH)$—$CH_2$—CH=CH—$(CH_2)_8$—$CH_3$, —$CH_2CH(COOMe)$— $CH_2$—CH=CH—$(CH_2)_8$—$CH_3$.

The present invention also relates to processes for preparing the compounds of general formula I.

The invention relates to a process for preparing $C^3$-derivatives of vinca alkaloid, wherein:

(a) the hydrazide of formula:

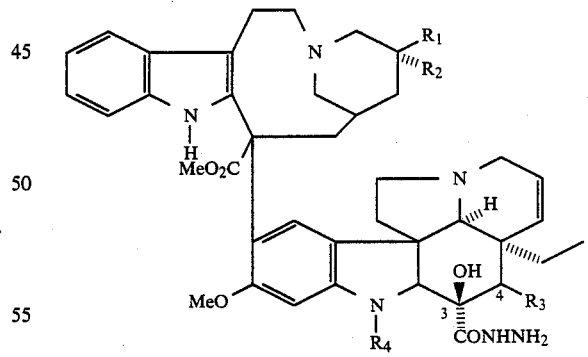

is reacted with a nitrite to form the corresponding azide at the $C^3$-position, and (b) the azide is reacted with an amine of formula:

H—A—$R'_5$ in which A and $R'_5$ have the meanings given above, but A is other than —O—, to obtain the desired compound.

The reaction scheme is thus as follows:

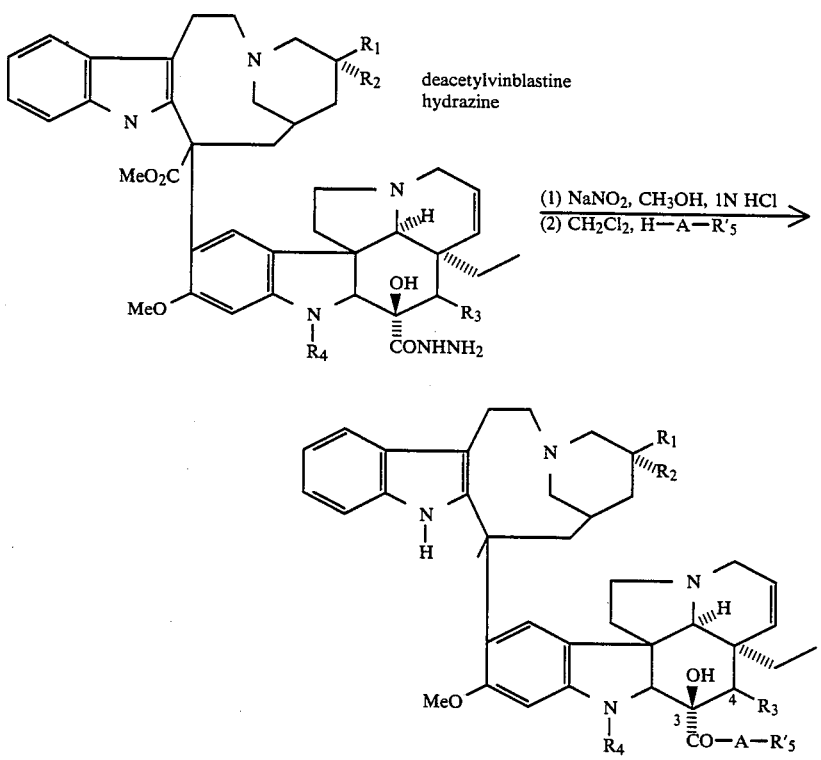

The reaction is performed in two stages; the hydrazide is dissolved in a solvent such as MeOH in acid medium, for example 1N HCl, the solution is cooled and a nitrite such as sodium nitrite is added, the pH is then adjusted with a weak base such as sodium hydrogen carbonate, and an acid azide is thereby obtained which is extracted with an immiscible solvent such as dichloromethane.

After separation, the dried and concentrated azide is treated with the amine corresponding to the desired product (H—A—R′5), and the crude product is separated from the reaction mixture and optionally purified.

The amide obtained is separated from the reaction medium by any suitable procedure.

In some cases, the side cahin can contain an asymmetric carbon atom; the invention then relates both to the compound in the form of a mixture of stereoisomers, for example the racemic mixture, and to the isomers in purified form.

According to a more special embodiment, the azide is reacted with an ester or an amide of formula H—A-′—R″5 in which A′ and R″5 have the meanings given above.

In effect, since A′ terminates in

A′—R″5 comprises

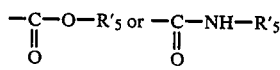

according to whether R″5 denotes O—R′5 or NH—R′5, respectively.

The invention also relates to the application of compounds of formula I by way of a drug, and also to the pharmaceutical compositions which incorporate them and contain excipients, supports or vectors which are pharmaceutically acceptable.

The compounds according to the present invention possess, in effect, antineoplastic properties which make them especially advantageous in the treatment of malignant neoplasias such as leukemias, generalized Hodgkin's disease, some lymphomas, sarcomas or carcinomas, in particular.

The activity of these compounds may, of course, vary depending on the structure, and the information given above is only for guidance.

The compositions according to the invention are preferably injectable compositions, especially compositions which can be administered intravenously.

These compositions can be produced by any process known in the field of vinca derivatives; in particular, the products can be dissolved in salt form in physiological saline containing, where appropriate, excipients which give a correct pH for the injectable solution.

These compositions can also be packaged in the form of two separate packs, lyophilisate of VLB derivatives and physiological solution, the mixing being performed at the time of the injection.

It is also possible to provide more complex galenical forms, utilizing the lipophilic nature of these molecules and turning to good account other pharmaceutically acceptable vectors.

The doses to be employed will depend on the product, the type of tumor to be treated and the patient's state; in the treatment of neoplasias, the dosage is always adapted by the practitioner.

Thus, it is common to use increasing doses in the treatment with vinca alkaloids, but this type of treatment has to take into account the changes in other physiological parameters of the patient, and sometimes has to be interrupted.

Under these conditions, it is not possible to provide dosages at this stage of the investigation.

The examples which follow are intended to demonstrate other characteristics and advantages of the present invention.

EXAMPLE 1

Preparation of 4-deacetylvinblastine-$C^3$-(N-dodecylcarboxamide) (compound No. 91)

Deacetylvinblastine hydrazide [CONRAD et al. J. Med. chem. 22,391 (1979)] is dissolved in the proportion of 0.500 g (0.65 millimole) in a mixture containing 10 ml of methanol and 30 ml of 1N HCl. The solution is cooled to 0° C. and is then treated with 0.103 g of dry $NaNO_2$ (1.49 millimole) in a single portion and with stirring. After 13 minutes, the pH of the solution is adjusted to 8.5 with cold saturated $NaHCO_3$ solution.

The deacetylvinblastine acid azide is rapidly extracted with 4×15 ml of $CH_2Cl_2$, and then washed with saturated NaCl solution.

The extracts are dried over $Na_2SO_4$ and concentrated to a volume of 20 ml. Dodecylamine in an amount of 0.500 g (2.69 millimoles) is added to the $CH_2Cl_2$ solution, and the solution is stirred for 2 hours at room temperature. Thin layer chromatography reveals a major component (Rf=0.73; silica; methanol/methylene chloride, 1:9).

The solvent is evaporated off and the residue chromatographed on silica, eluting with methylene chloride/methanol, first with 96:4 and then 93:7. The appropriate fractions are combined and the solvents removed to lead to 365 mg of 4-deacetylvinblastine-$C^3$-(N-dodecylcarboxamide) (yield: 61%), with the following physical properties:

Rf: 0.73 (silica; $CH_2Cl_2/CH_3OH$, 90:10)

MS: (DCI, isobutane): 922 ($M^+ +1$), 935 ($M^+ +14$), 826, 272, 186

NMR: ($CDCl_3$, 360 MHz): 9.50 (m, OH), 8.02 (s, 1H, NH), 7.51 (d, 1H, H'$_9$), 6.57 (s, 1H, H$_9$), 6.05 (S, 1H, H$_{12}$), 5.80 (s, 2H, H$_{14}'$, H$_{15}'$), 4,16 (d, 1H, H$_{17}$), 3.95 (m, H$_{17a}'$), 3.76 (s, 3H, $CH_3O$), 3.59 (s, 3H, $CH_3O$), 3.36 (s, 1H, H$_2$), 2.79 (S, 3H, $CH_3$—N), 2.60 (s, 1H, H$_{21}$), 1.37–1.20 (m, 25H), 1.02–0.77 (m, $3CH_3 + H_{14}$)

IR: (KBr, $cm^{-1}$) 3420, 1665, 1730 $cm^{-1}$.

The bis(methanesulfonate) salt is prepared by dissolving vinblastine-$C^3$-(N-dodecylcarboxamide) (100 mg) in anhydrous ethanol and adding 2% strength ethanolic methanesulfonic acid. The solution is concentrated under vacuum. 3 ml of distilled water are added to the residue and the solution obtained is lyophilized to give 123 mg of bis(methanesulfonate) salt.

IR: (KBr): 3400, 2923, 2858, 1729, 1658, 1612, 1503, 1760, 1040 $cm^{-1}$.

EXAMPLE 2

Preparation of 4-deacetylvinblastine-$C^3$-(N-oleylcarboxamide) (compound No. 252)

Following the procedure described above, 0.500 g of 4-deacetylvinblastine hydrazide (0.65 millimole) is reacted with 0.695 g of oleylamine (2.6 millimoles) to give 4-deacetylvinblastine-$C^3$-(N-oleylcarboxamide) (0.310 g; yield: 47%), having the following properties:

Rf: 0.72; silica; methanol/methylene chloride, 1:9

MS (DCI, isobutane), 1005 ($M^+ +1$), 922, 810, 733, 302, 392, 279.

IR: (KBr): 3460, 2920, 2858, 1735, 1663, 1612, 1502, 1460, 1430 $cm^{-1}$

NMR: ($CDCl_3$, 360 MHz): 9.52 (OH), 8.00 (NH), 7.62 (H-9'), 7.17–7.05 (H-10', H-11', H-12'), 6.60 (H-9), 6.05 (H-12), 5.81 (H-14', H-15'), 5.35 (—HC=CH—), 4.17 (H-17), 3.95 (H-17A'), 3.77 (OMe), 3.58 (OMe), 3.36 (H-2), 2.78 (N—Me), 2.60 (H-21), 0.97–0.81 (3Me).

EXAMPLE 3

Preparation of 4-deacetylvinblastine-$C^3$-(N-octadecylcarboxamide)

Following the prodecure described above, 4-deacetylvinblastine-$C^3$-(N-octadecylcarboxamide) is prepared starting with 0.500 g of deacetylvinblastine hydrazide (0.65 millimole) and 0.700 g of octadecylamine (2.59 millimoles). 0.332 g of 4-deacetylvinblastine-$C^3$-(N-octadecylcarboxamide) is obtained (yield: 51%).

This compound possesses the following physical properties:

Rf: 0.67; methylene chloride/methanol, 93:7

IR: (KBr, $cm^{-1}$), 3410, 2920, 2854, 1739, 1663, 1616, 1503, 1460, 1431 $cm^{-1}$

MS: (DCI, $NH_3$), 1007 ($M^+ +1$), 974, 960, 946

NMR: ($CDCl_3$, 360 MHz): 9.52 (OH), 8.00 (NH), 7.52 (H-9'), 7.17–7.07 (H10', H11' H12'), 6.57 (H-9), 6.05 (H-12), 5.82 (H-14', H-15'), 4.17 (H-17), 3.95 (H-17A'), 3.77 (O—Me), 3.57 (OMe), 3.35 (H-2), 2.80 (N—Me), 2.61 (H-21), 1.37–1.17 (18$CH_2$), 0.97–0.82 (3Me).

EXAMPLE 4

Preparation of 4-deacetylvinblastine-$C^3$-[N-(12-aminododecyl)carboxamide] (compound No. 182)

Following the general procedure, 0.500 g of deacetylvinblastine hydrazide (0.65 millimole) is converted to 0.327 g of 4-deacetylvinblastine-$C^3$-[N-(12-aminododecyl)carboxamide] by reaction with 0.500 g of 1,12-diaminododecane (2.50 millimoles). The compound is purified by chromatography on alumina, the elution being performed with methylene chloride/methanol, 92:8. The compound is isolated as an amorphous powder having the following properties:

Rf: 0.38; alumina; methanol/methylene chloride 10:90

NMR: ($CDCl_3$, 360 MHz), δ: 9.52 (m, OH), 8.01 (m, N—H), 7.51 (d, 1H, H$_9$), 6.58 (s, 1H, H$_9$), 6.05 (s, 1H, H$_{12}$), 5.81 (s, 2H, H$_{15}'$, H$_{14}'$), 4.15 (d, 1H, H-17 ), 3.76 (s, 3H, $CH_3O$), 3.95 (m, 1H, H$_{17A'}$), 3.59 (s, 3H, $CH_3O$), 3.55 (s, 1H, H$_2$), 2.77 (s, 3H, N—$CH_3$), 2.60 (s, 1H, H$_{21}$), 2.25 (m, 1H, H$_{17'}$), 1.35–1.24 (m, 23H), 1.00–0.82 (m, 7H, $2CH_3 + H_{14'}$).

MS: (DCI, isobutane) 938 ($M^+ +1$), 965 ($M^+ +28$), 923 ($M^+ -14$), 938, 279

IR: (KBr): 3460, 2920, 2853, 1730, 1663, 1605, 1502, 1410, 1225 $cm^{-1}$.

EXAMPLE 5

Preparation of 4-palmitoyloxy-4-deacetylvinblastine 0.500 g of 4-deacetylvinblastine (0.65 millimole) and 0.119 g of 4-dimethylaminopyridine (0.975 millimole) are dissolved in 10 ml of methylene chloride and the solution is then cooled to 0° C. 0.214 g of palmitoyl chloride (0.78 millimole) is added while mixing.

Thin layer chromatography after 24 h reveals the presence of a major component [silica; ether/(CH$_3$OH/NH$_3$), 92:8]. The solvent is evaporated off. The residue is introduced into a column of silica and eluted with CH$_2$Cl$_2$/CH$_3$OH, 93:7.

The appropriate fractions are collected and evaporated yielding 323 mg of 4-palmitoyloxy-4-deacetylvinblastine (yield: 49%).

Physical properties:

Rf: 0.65 (silica; CH$_2$Cl$_2$/CH$_3$OH, 90:10)

IR (KBr): 3465, 2920, 2855, 1739, 1613, 1500, 1460, 1431, 1362, 1242, 1223 cm$^{-1}$

MS: DCI (isobutane) 1008 (M$^+$+1), 990, 958, 756, 586, 512, 413, 256.

NMR: (360 MHz CDCl$_3$) 8.02 (NH), 7.52 (H-9'), 7.17–7.10 (H-10', H-11', H-12'), 6.60 (H-9), 6.08 (H-12), 5.82 (H-14'), 5.46 (H-17), 5.28 (H-15'), 3.97 (H-17A'), 3.77 (OMe), 3.76 (OMe), 3.68 (H-2), 3.60 (OMe) 2.71 (N—Me), 2.66 (H-21), 1.36–1.21 (16×CH$_2$), 0.93–0.76 (3×CH$_3$).

EXAMPLE 6

Preparation of dodecyl N-(O$^4$-deacetyl-23-vinblastinoyl)-L-isoleucinate (compound No. 860)

In Examples 6 to 11, A' and R''$_5$ correspond to the compounds in the following table:

| A' (originating from) | R''$_5$ | Compound No. |
| --- | --- | --- |
| Ile | —O—(CH$_2$)$_{11}$—CH$_3$ | 860 |
| Ile | —HN—(CH$_2$)$_{11}$—CH$_3$ | 720 |
| Ile | —HN—(CH$_2$)$_9$—CH$_3$ | 1370 |
| Trp | —HN—(CH$_2$)$_9$—CH$_3$ | 1440 |
| Trp | —HN—(CH$_2$)$_{11}$—CH$_3$ | 1470 |
| Gly—Phe | —HN—(CH$_2$)$_{11}$—CH$_3$ | 1590 |

Deacetylvinblastine hydrazide [CONRAD et al., J. Med. chem. 22,931 (1979)] is dissolved in the proportion of 0.500 g (0.65 millimole) in a mixture containing 10 ml of methanol and 30 ml of 1N HCl. The solution is cooled to 0° C. and is then treated with 0.103 g of dry NaNO$_2$ (1.49 millimole) in a single portion and with stirring. After 13 minutes, the pH of the solution is adjusted to 8.5 with cold saturated NaHCO$_3$ solution.

The deacetylvinblastine acid azide is rapidly extracted with 4×15 ml of CH$_2$Cl$_2$, and then washed with saturated NaCl solution.

The extracts are dried over Na$_2$SO$_4$ and concentrated to a volume of 20 ml. L-isoleucine dodecyl ester in an amount of 0.500 g is added to the CH$_2$Cl$_2$ solution, and the solution is stirred for 2 hours at room temperature.

The solvents are removed and dodecyl N-(O$^4$-deacetyl-23-vinblastinoyl)-L-isoleucinate is obtained. The physical properties as follows:

IR (KBr, cm$^{-1}$): 3460, 3410, 2958, 2930, 2858, 1737, 1670, 1615, 1502, 1459, 1221, 1010, 740;

MS: (DCI, acetone): 1037 (M$^+$+1), 1051 (M$^+$+14+1);

NMR: (CDCl$_3$), 360 MHz): δ 9.36 (OH), 7.97 (NH), 7.46 (H-9', H-10'), 7.10 (H-11', H-12'), 6.53 H-12), 6.01 (H-9), 5.81 (H-14), 5.75 (H-15), 4.58 (CH*), 4.17 (H-17, CH$_3$—O), 3.93 (H-17A'), 3.73 (O—CH$_3$), 3.57 (O—CH$_3$), 3.45 (H-2), 2.86 (H-21A'), 2.81 (H-21B'), 2.71 (N—CH$_3$), 2.55 (H-21, 2.42 (H-3B'), 2.36 (OH-17), 2.02 (H-6A), 1.91 (H-6B), 1.25 (12×CH$_2$), 0.85–0.95 (5×CH$_3$).

EXAMPLE 7

Preparation of N-[N-(O$^4$-deacetyl-23-vinblastinoyl)-L-isoleucyl]-dodecylamine (compound 720)

In the same manner, the compound 720 was prepared from deacetylvinblastine hydrazide and L-isoleucine dodecylamide.

Its physical properties are as follows:

IR: (KBr, cm$^{-1}$): 3460, 2960, 2924, 2855, 1739, 1720, 1658, 1616, 1503, 1460, 1432, 1223, 1009, 740;

MS: (DCI, acetone): 1036 (M$^+$+1), 1050 (M$^+$+14+1), 1064 (M+30 28+1);

NMR: (CDCl$_3$, 360 MHz): δ 9.38 (OH), 7.98 (NH), 7.46 (H-9', H-10'), 7.10 (H-11', H-11', H-12), 6.54 (H-12), 6.01 (H-9), 5.96 (tr), 5.80 (H-14), 5.75 (H-15), 4.12 (H-17+m), 3.95 (H-17A'), 3.76 (O—CH$_3$), 3.58 (O—CH$_3$), 3.47 (H-2), 2.86 (H-21A'), 2.83 (H-21B'), 2.71 (N—CH$_3$), 2.57 (H-21), 2.41 (H-3B'), 2.01 (H-6A), 1.87 (H-6B), 1.26 (12×CH$_2$), 0.86–0.97 (5×CH$_3$).

EXAMPLE 8

Preparation of N-[N-(O$^4$-deacetyl-23-vinblastinoyl)-L-isoleucyl]-decylamine (compound 1370)

The reaction between deacetylvinblastine hydrazide and L-isoleucine decylamide according to the procedure of Example 1 leads to the compound 1370, which has the following physical properties:

IR: (KBr, cm$^{-1}$): 3464, 2960, 2927, 2880, 2858, 1738, 1720, 1655, 1615, 1502, 1458, 1431, 1221, 738.

MS: (DCI, acetone): 1008 (M$^+$+1), 1022 (M$^+$+14+1).

NMR: (CDCl$_3$, 360 MHz): 8.00 (NH), 7.50 (H-9', H-10'), 7.10 (H-11', H-12'), 6.55 (H-12), 6.05 (H-9), 5.93 (tr), 5.81 (H-14), 5.75 (H-15), 4.13 (H-17+m), 3.96 (H-17A'), 3.76 (OCH$_3$), 3.60 (O—CH$_3$), 3.45 (H-2), 2.71 (N—CH$_3$), 2.57 (H-21), 2.42 (H-3B'), 1.26 (10×CH$_2$), 0.83–0.95 (5×CH$_3$).

EXAMPLE 9

Preparation of N-[N-(O$^4$-deacetyl-23-vinblastinoyl)-L-tryptophyl]-dodecylamine (compound 1470)

Following the procedure described in Example 1, the compound 1470 is prepared starting with deacetylvinblastine hydrazide and L-tryptophan dodecylamide. This compound has the following physical properties:

IR: (KBr, cm$^{-1}$): 3400, 2921, 2857, 1737, 1718, 1660, 1606, 1500, 1409, 1224, 1010, 738.

MS: (DCI, acetone): 1109 (M$^+$+1), 1123 (M$^+$+14+1);

NMR: (CDCl$_3$, 360 MHz): 8.17 (NH, s), 8.02 (NH, s), 7.80 (1H, d), 7.73 (1H, d), 7.52 (1H, d), 7.35 (1H, d), 7.21–7.02 (m, 5H), 6.59 (H-12), 6.05 (H-9), 5.80 (H-14, H-15), 5.52 (tr, 1H), 4.62 (m, 1H), 4.16 (H-17), 3.96 (H-17'), 3.75 (OMe), 3.60 (OMe), 3.48 (H-2), 2.82 (H-21A'), H-21B'), 2.72 N—Me), 2.60 (H-21), 1.12–1.35 (12×CH$_2$), 0.83–1.02 (3×CH$_3$).

EXAMPLE 10

Preparation of N-[N-(O$^4$-deacetyl-23-vinblastinoyl)-L-tryptophyl]-decylamine (compound 1440)

In the same manner, the compound 1440 was prepared from deacetylvinblastine hydrazide and L-tryptophan decylamide. This compound possesses the following physical properties:

IR: (KBr, cm$^{-1}$): 3400, 2922, 2858, 1720, 1659, 1608, 1500, 1460, 1430, 1225, 1010, 740;

MS: (DCI, acetone): 1081 (M$^+$), 1095 (M$^+$+14), 1109 (M$^+$+28);

NMR: (CDCl$_3$, 360 MHz): 8.20 (NH, s), 8.02 (NH, s), 7.80 (1H, d); 7.73 (1H, d), 750 (1H, d), 7.34 (1H, d), 7.21-7.02 (5H, m), 6.58 (H-12, s), 6.04 (H-9, s), 5.78 (H-14, H-15), 5.52 (tr), 4.61 (m, 1H), 4.17 (H-17), 3.93 (H-17A'), 3.75 (OMe), 3.47 (H-2), 2.82 (H-21A'-H-21B'), 2.72 (N—Me), 2.60 (H-21), 1.37-1.10 (10×CH$_2$), 0.80-1.01 (3×CH$_3$).

EXAMPLE 11

Preparation of N-{[N-(O$^4$-deacetyl-23-vinblastinoyl)-L-glycyl]-L-phenylalanyl}dodecylamine (compound 1590)

Following the procedure described in Example 1, the compound 1590 is prepared from deacetylvinblastine hydrazine and L-glycyl-L-phenylalanine dodecylamide. Its physical properties are as follows:

IR: (KBr, cm$^{-1}$): 3400, 2925, 2857, 1720, 1658, 1615, 1500, 1457, 1227, 740;

MS: (DCI, acetone): 1127 (M$^+$+1), 1141 (M$^+$+14+1);

NMR: (CDCl$_3$, 360 MHz): 8.02 (NH, s), 7.77 (m, 1H), 7.50 (d, 1H), 7.31-7.05 (m, 5H), 6.57 (H-9), 6.07 (H-12), 5.77 (H-14, H-15), 5.62 (tr, 1H), 4.52 (m, 1H), 3.96 (H-17A'), 4.17 (H-17), 3.76 (OMe), 3.60 (OMe), 3.47 (H-2), 2.85 (H-21A'-H-21B'), 2.77 (N—Me), 2.62 (H-21), 1.13-1.40 (12×CH$_2$), 0.85-0.98 (3×CH$_3$).

EXAMPLE 12

Antitumor activity

Trials for antitumor activity of the VLB derivatives according to the present invention of Examples 1 to 5 were performed on mice in the following manner.

12.1 Parameters of activity

Two parameters of activity are used:
the parameter "ILS" represents the increase in the length of life, as a percentage and according to the following relationship:

$$ILS = \frac{T - C}{C} \times 100$$

T (in days) being the mean length of life of the treated mice,

C (in days) being the mean length of life of the control mice;

the parameter ("long-term survivors", the calculation of which as a percentage is performed on day 60.

12.2 Intravenous administration

Female DBA$_2$ mice were inoculated intravenously on day 0 with 10$^5$ P$_{388}$ leukemia cells. On the following day, the compound 91 according to the invention is administered intravenously.

| Dose (mg/kg/d) | ILS (%) | Survivors day 60 (%) |
|---|---|---|
| 6.25 | 1 | 0 |
| 12.5 | 1 | 0 |
| 25 | 14 | 0 |
| 50 | 45.9 | 0 |
| 100 | 129 | 0 |
| 150 | 167 | 14 |
| 175 | −25 | |
| 200 | −43 | 0 |

A very significant activity of the compound No. 91 is noted at the doses of 100 and 150 mg/kg/d.

12.3 Intraperitoneal administration 6 female BDF$_1$ mice are inoculated intraperitoneally on day 0 with 10$^6$ P$_{388}$ leukemia cells. On the following day, the compound 91 is administered intraperitoneally.

| Dose (mg/kg/d) | ILS (%) | Survivors day 60 (%) |
|---|---|---|
| 12.5 | 57 | 0 |
| 25 | 65 | 0 |
| 50 | 77 | 0 |
| 100 | 148 | 0 |
| 150 | — | |
| 200 | 59 (toxic) | 0 |

As in Example 12.2 the compound is seen to show very significant activity.

EXAMPLE 13

Chemotherapeutic activity of the compounds of Examples 6 to 11

Female DBA$_2$ mice are inoculated intravenously with P$_{388}$ leukemia cells. On the following day, the designated compound is administered.

| Number of P$_{388}$ cells | Scheme | Compound No. | Dose (mg/kg/d) | ILS* (%) | Survivors day 60 |
|---|---|---|---|---|---|
| 10$^5$ | i.v./i.v. | 860 | 100 | 131 | 3/10 |
| 10$^5$ | i.v./i.v. | 720 | 200 | 57 | 0/10 |
| 10$^6$ | ip/ip | | | | |
| 10$^6$ | ip/ip | 91 | 150 | 213 | 0/10 |
| 10$^6$ | ip/ip | 860 | 50 | 155 | — |
| 10$^6$ | ip/ip | 860 | 100 | 172 | — |
| 10$^6$ | ip/ip | 860 | 200 | 253 | — |

*ILS represents the increase in the length of life, as a percentage and according to the following relationship:

$$ILS \% = \frac{T - C}{C} \times 100$$

T (in days) being the mean length of life of the treated mice,
C (in days) being the mean length of life of the control mice.

EXAMPLE 14

Influence of the chain length on the activity and the toxicity

The table below shows a very substantial effect on the activity and the toxicity of the derivatives according to the invention.

It is observed that the increase in the chain length gives rise to:
a 10- to 30-fold decrease in the toxicity,
an increase in the activity,
long-term survivors.

The products were injected at their optimal dose.

The compounds VDS and No. 1610 correspond to short chains:

| | |
|---|---|
| VDS (vindesine) | $R_5 = NH_2$ |
| No. 1610 | $R_5 = NH-(CH_2)_5-CH_3$ |

The compounds Nos. 850 and 91 correspond to derivatives according to the invention:

| | |
|---|---|
| No. 850 | $R_5 = NH-(CH_2)_9-CH_3$ |
| No. 91 | $R_5 = NH-(CH_2)_{11}-CH_3$ |

| NUMBER OF $P_{388}$ CELLS | INOCULATION SCHEME | TREATMENT SCHEME | PRODUCT | DOSE mg/kg | NUMBER OF MICE | ILS % | SURVIVORS (day 60) |
|---|---|---|---|---|---|---|---|
| $10^5$ | i.v. | i.v. (d 1) | VDS | 4 | 10 | 43 | 0/10 |
| | | | 1610 | 3.13 | 7 | 74 | 0/7 |
| | | | 850 | 50 | 9 | 112 | 2/9 |
| | | | 91 | 150 | 7 | 167 | 1/7 |
| $10^6$ | i.p. | i.p. (d 1) | VDS | 2.5 | 11 | 150 | 0/11 |
| | | | | 3 | 10 | 89 | 0/10 |
| | | | 91 | 150 | 10 | 213 | 0/10 |

The presence of a long fatty chain favors the antitumor activity of the vinca derivatives by permitting a synergistic effect between the lysosomotropic activity of the detergent and the therapeutic activity of the vinblastine.

In addition, the presence of a long fatty chain causes increased lipophilia and makes possible a different bioavailability of these vinca derivatives, endowing these medicinal substances, inter alia, with properties which provide for preferential resorption via the lymph ducts of the small intestine at the expense of that via the bloodstream.

We claim:

1. Vinca (indoledihydroindole) alkaloid compounds of formula I:

(I)

in which
($R_1$, $R_2$) is (—Et, —OH), or (—H, Et),
$R_4$ is —H, —Me or —CHO,
$R_3$ is —OH or $$-O-C-R'_3$$
$$\parallel$$
$$O$$

$R_5$ is —A—R'$_5$, A being chosen from —NH— and —O—,

R'$_3$ and R'$_5$ are hydrocarbon groups having from 1 to 20 carbon atoms, at least one of R'$_3$ and R'$_5$ being an alkyl or alkenyl group having at least 10 aliphatic carbon atoms, the hydrocarbon groups being unsubstituted or substituted with one or more amino, di($C_1$-$C_3$ alkyl)amino, mono-($C_1$-$C_3$ alkyl)amino, $NH(CH_2$-$C_5$ alkanoyl), cyano, COOH, S($C_1$-$C_3$ alkyl), COO($C_1$-$C_3$ alkyl) or COO-aryl radicals.

2. Compounds as claimed in claim 1, in which:
$R_3$ is —OH,
$R_5$ is —AR'$_5$ with A being —NH—, and
R'$_5$ is a $C_{10}$ to $C_{20}$ alkyl radical or alkenyl radical which is unsubstituted or substituted with one or more amino, COOH, or COO($C_1$-$C_3$ alkyl) radicals.

3. Compounds as claimed in claim 2, in which R'$_5$ is chosen from —$(CH_2)_{11}$—$CH_3$, —$(CH_2)_{17}$—$CH_3$, —$(CH_2)_{12}$—$NH_2$ and —$(CH_2)_7$—CH=CH—$(CH_2)_8$—$CH_3$.

4. Compounds as claimed in claim 2, in which R'$_5$ is a $C_7$ to $C_{20}$ n-alkyl or n-alkenyl radical and A is a protected or unprotected divalent radical of an amino acid which participates in the constitution of proteins.

5. Compounds as claimed in claim 1, in which, in the formula I:
$R_5$ is —OMe,
$R_3$ is $$-O-C-R'_3,$$
$$\parallel$$
$$O$$

with R'$_3$,
being a $C_{10}$ to $C_{20}$ alkyl or alkenyl radical which is unsubstituted or substituted with one or more amino, COOH, or COO($C_1$-$C_3$alkyl) radicals.

6. Compounds as claimed in claim 5, in which R'$_3$ is chosen from: —$(CH_2)_{14}$—$CH_3$, —$CH_2CH(COOH)$—$CH_2$—CH=CH—$(CH_2)_8$—$CH_3$ or —$CH_2CH(COOMe)$—$CH_2$—CH=CH—$(CH_2)_8$—$CH_3$.

7. An antitumor pharmaceutical composition, which contains an effective antitumor amount of a vinca alkaloid compound as claimed in claim 1, with an excipient, support or vector which is pharmaceutically acceptable.

* * * * *